(12) United States Patent
Pianca et al.

(10) Patent No.: US 8,694,127 B2
(45) Date of Patent: Apr. 8, 2014

(54) SYSTEMS AND METHODS FOR MAKING AND USING RADIALLY-ALIGNED SEGMENTED ELECTRODES FOR LEADS OF ELECTRICAL STIMULATION SYSTEMS

(75) Inventors: Anne Margaret Pianca, Santa Monica, CA (US); Priya Sundaramurthy, Fremont, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 84 days.

(21) Appl. No.: 13/226,159

(22) Filed: Sep. 6, 2011

(65) Prior Publication Data
US 2012/0071949 A1 Mar. 22, 2012

Related U.S. Application Data

(60) Provisional application No. 61/385,080, filed on Sep. 21, 2010.

(51) Int. Cl.
*A61N 1/05* (2006.01)
(52) U.S. Cl.
USPC ............ 607/117; 607/116; 607/118; 607/119
(58) Field of Classification Search
USPC .................................................. 607/116–119
See application file for complete search history.

(56) References Cited

U.S. PATENT DOCUMENTS

| 4,602,624 A | 7/1986 | Naples et al. |
|---|---|---|
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |

(Continued)

FOREIGN PATENT DOCUMENTS

| EP | 0580928 A1 | 2/1994 |
|---|---|---|
| EP | 0650694 B1 | 7/1998 |

(Continued)

OTHER PUBLICATIONS

U.S. Appl. No. 13/275,112, filed Oct. 17, 2011.

(Continued)

*Primary Examiner* — Joseph Stoklosa
(74) *Attorney, Agent, or Firm* — Frommer Lawrence & Haug LLP; Patrick R. Turner

(57) ABSTRACT

An electrical stimulation lead includes a lead body insertable into a patient. Electrodes are disposed along the lead body. The electrodes include at least two sets of segmented electrodes. Each set of segmented electrodes includes a first segmented electrode and a second segmented electrode radially spaced apart from one another around a circumference of the lead body. A tab is disposed on the first segmented electrode of each set of segmented electrodes. The tabs extend into the lead body. A guide feature is disposed on the tabs. The guide features are each radially aligned with one another along the length of the lead body. Conductors extend along the length of the lead body from a proximal end to the electrodes. Each of the conductors is electrically coupled to at least one of the electrodes. At least one of the conductors extends through the radially-aligned guide features of the tabs.

10 Claims, 12 Drawing Sheets

(56) References Cited

U.S. PATENT DOCUMENTS

| | | | |
|---|---|---|---|
| 5,711,316 | A | 1/1998 | Elsberry et al. |
| 5,713,922 | A | 2/1998 | King |
| 5,800,350 | A | 9/1998 | Coppleson et al. |
| 5,843,148 | A | 12/1998 | Gijsbers et al. |
| 5,938,688 | A | 8/1999 | Schiff |
| 5,987,361 | A | 11/1999 | Mortimer |
| 6,018,684 | A | 1/2000 | Bartig et al. |
| 6,134,478 | A | 10/2000 | Spehr |
| 6,161,047 | A | 12/2000 | King et al. |
| 6,167,311 | A | 12/2000 | Rezai |
| 6,322,559 | B1 | 11/2001 | Daulton et al. |
| 6,510,347 | B2 | 1/2003 | Borkan |
| 6,556,873 | B1 | 4/2003 | Smits |
| 6,564,078 | B1 | 5/2003 | Marino et al. |
| 6,678,564 | B2 | 1/2004 | Ketterl et al. |
| 6,757,970 | B1 | 7/2004 | Kuzma et al. |
| 7,027,852 | B2 | 4/2006 | Helland |
| 7,047,084 | B2 * | 5/2006 | Erickson et al. ............ 607/116 |
| 7,292,890 | B2 | 11/2007 | Whitehurst et al. |
| 7,489,971 | B1 | 2/2009 | Franz |
| 7,668,601 | B2 | 2/2010 | Hegland et al. |
| 7,761,985 | B2 | 7/2010 | Hegland et al. |
| 7,809,446 | B2 | 10/2010 | Meadows |
| 7,840,188 | B2 | 11/2010 | Kurokawa |
| 7,860,570 | B2 | 12/2010 | Whitehurst et al. |
| 7,974,705 | B2 | 7/2011 | Zdeblick et al. |
| 7,979,140 | B2 | 7/2011 | Schulman |
| 8,000,808 | B2 | 8/2011 | Hegland et al. |
| 8,019,440 | B2 | 9/2011 | Kokones et al. |
| 8,036,755 | B2 | 10/2011 | Franz |
| 8,041,309 | B2 | 10/2011 | Kurokawa |
| 8,099,177 | B2 | 1/2012 | Dahlberg |
| 8,225,504 | B2 | 7/2012 | Dye et al. |
| 8,295,944 | B2 | 10/2012 | Howard et al. |
| 2002/0156513 | A1 | 10/2002 | Borkan |
| 2002/0183817 | A1 | 12/2002 | Van Venrooij et al. |
| 2004/0019372 | A1 * | 1/2004 | Cole ............................ 607/116 |
| 2005/0015130 | A1 | 1/2005 | Gill |
| 2005/0038489 | A1 | 2/2005 | Grill |
| 2005/0171587 | A1 | 8/2005 | Daglow et al. |
| 2006/0025841 | A1 | 2/2006 | McIntyre |
| 2006/0247697 | A1 | 11/2006 | Sharma et al. |
| 2007/0150036 | A1 | 6/2007 | Anderson |
| 2007/0203546 | A1 | 8/2007 | Stone et al. |
| 2008/0103580 | A1 | 5/2008 | Gerber |
| 2008/0114230 | A1 | 5/2008 | Addis |
| 2008/0215125 | A1 | 9/2008 | Farah et al. |
| 2008/0269854 | A1 * | 10/2008 | Hegland et al. ............ 607/116 |
| 2009/0187222 | A1 | 7/2009 | Barker |
| 2009/0204192 | A1 | 8/2009 | Carlton et al. |
| 2009/0204193 | A1 | 8/2009 | Kokones et al. |
| 2010/0036468 | A1 | 2/2010 | Decre et al. |
| 2010/0076535 | A1 | 3/2010 | Pianca et al. |
| 2010/0082076 | A1 | 4/2010 | Lee et al. |
| 2010/0094387 | A1 | 4/2010 | Pianca et al. |
| 2010/0268298 | A1 | 10/2010 | Moffitt et al. |
| 2011/0005069 | A1 | 1/2011 | Pianca |
| 2011/0047795 | A1 | 3/2011 | Turner et al. |
| 2011/0056076 | A1 | 3/2011 | Hegland et al. |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0131808 | A1 | 6/2011 | Gill |
| 2011/0238129 | A1 | 9/2011 | Moffitt et al. |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0203320 | A1 * | 8/2012 | DiGiore et al. ............ 607/148 |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009/102536 A1 | 8/2009 |

OTHER PUBLICATIONS

U.S. Appl. No. 13/363,059, filed Jan. 31, 2012.
U.S. Appl. No. 13/368,982, filed Feb. 8, 2012.
U.S. Appl. No. 13/369,013, filed Feb. 8, 2012.
U.S. Appl. No. 13/368,733, filed Feb. 8, 2012.
International Search Report and Written Opinion mailed Jul. 20, 2012 for PCT/US2011/050530.
U.S. Appl. No. 12/177,823, filed Jul. 22, 2008.
U.S. Appl. No. 13/787,171, filed Mar. 6, 2013.
U.S. Appl. No. 13/750,725, filed Jan. 25, 2013.
U.S. Appl. No. 13/899,316, filed May 21, 2013.
U.S. Appl. No. 13/906,776, filed May 31, 2013.
U.S. Appl. No. 13/951,057, filed Jul. 25, 2013.

* cited by examiner

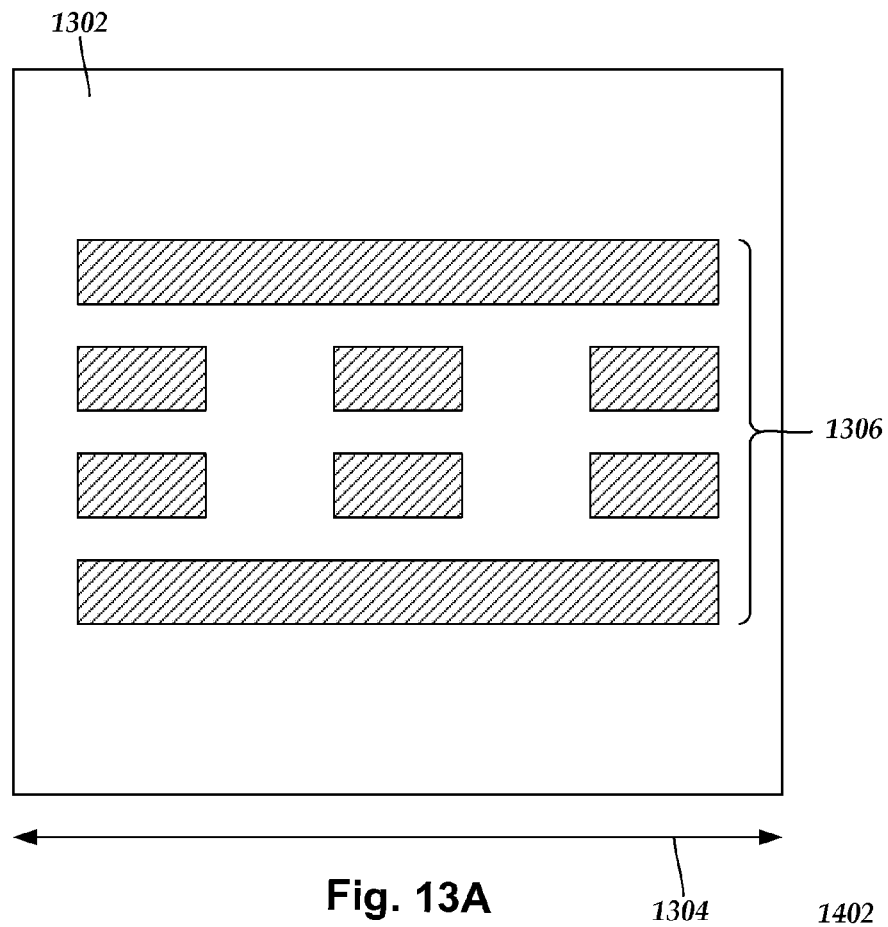
Fig. 13A
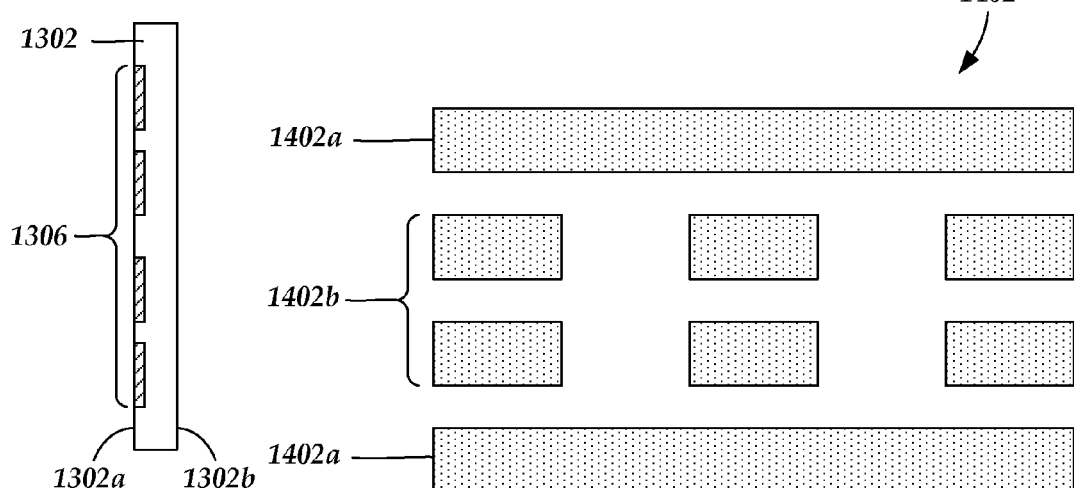
Fig. 13B
Fig. 14

SYSTEMS AND METHODS FOR MAKING AND USING RADIALLY-ALIGNED SEGMENTED ELECTRODES FOR LEADS OF ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/385,080 filed on Sep. 21, 2010, which is incorporated herein by reference.

FIELD

The invention is directed to the area of electrical stimulation systems and methods of making and using the systems. The present invention is also directed to electrical stimulation leads with multiple sets of radially-aligned segmented electrodes, as well as methods of making and using the segmented electrodes, leads, and electrical stimulation systems.

BACKGROUND

Electrical Stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, an electrical stimulation lead includes an elongated lead body having a distal end, a proximal end, a length, a circumference, and an outer surface. The lead body is configured and arranged for insertion into a patient. A plurality of electrodes are disposed along the outer surface of the lead body. The plurality of electrodes includes at least two sets of segmented electrodes disposed at the distal end of the lead body. Each set of segmented electrodes includes a first segmented electrode and a second segmented electrode radially spaced apart from one another around the circumference of the lead body. A first tab is disposed on the first segmented electrode of each of the at least two sets of segmented electrodes. Each of the first tabs extends inwardly from the first segmented electrodes into the lead body. A guide feature is disposed on each of the first tabs. The guide features are each radially aligned with one another along the length of the lead body. A plurality of conductors extend along the length of the lead body from the proximal end to the plurality of electrodes. Each of the conductors is electrically coupled to at least one of the plurality of electrodes. At least one of the plurality of conductors extends through the radially-aligned guide features of the first tabs.

In another embodiments, a method of forming a lead for a stimulation device includes forming a plurality of pre-electrodes. Each of the pre-electrodes is formed in the shape of a ring. Each of the plurality of pre-electrodes comprises at least two thin-walled portions separated by at least two thick-walled portions. At least two of the plurality of pre-electrodes include a first tab disposed on one of the at least two thick-walled portions. Each of the first tabs includes a guide feature. The plurality of pre-electrodes are disposed near a distal end of a lead body. At least one conductor is joined to each thick-walled portion of each of the plurality of pre-electrodes such that at least one of the at least one conductor extends through each of the guide features, thereby radially aligning the guide features along a length of the lead body. The plurality of pre-electrodes are ground to remove the thin-walled portions of each of the plurality of pre-electrode to form a plurality of segmented electrodes from the thick-walled portions of each of the plurality of pre-electrodes.

In yet another embodiment, an electrical stimulation lead assembly includes an elongated lead body having a distal end, a proximal end, a length, a circumference, and an outer surface. The lead body is configured and arranged for insertion into a patient. A membrane is coupleable to the distal end of the lead body. The membrane includes a rear face coupleable to the lead body, a front face opposite to the rear face, and a width. When the membrane is coupled to the distal end of the lead body, the membrane is disposed over at least a portion of the outer surface of the distal end of the lead body such that the width of the membrane wraps around the circumference of the lead. A plurality of electrodes are disposed on the front face of the membrane. A plurality of conductors extend along the length of the lead body from the proximal end to the plurality of spaced-apart electrodes. Each of the conductors is electrically coupled to at least one of the plurality of electrodes.

In another embodiment, a method of forming a lead for a stimulation device includes disposing a plurality of electrodes along a front face of a membrane. A rear face of the membrane is coupled to an outer surface of a distal end of an elongated lead body such that the rear face of the membrane conforms to a shape of the outer surface of the lead body and a width of the membrane wraps around the outer surface of the lead body. Individual conductors extending along a length of the lead body are coupled to each of the plurality of electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 13A is a schematic top view of one embodiment of a membrane configured and arranged to couple to a lead, the membrane defining wells for receiving electrodes, according to the invention;

FIG. 13B is a schematic side view of one embodiment of the membrane of FIG. 13A, according to the invention;

FIG. 14 is a schematic top view of one embodiment of an array of electrodes configured and arranged for being disposed on the membrane of FIG. 13A, according to the invention;

DETAILED DESCRIPTION

The invention is directed to the area of electrical stimulation systems and methods of making and using the systems. The present invention is also directed to forming electrical stimulation leads with multiple sets of radially-aligned segmented electrodes, as well as methods of making and using the segmented electrodes, leads, and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Pat. No. 7,809,446("Devices and Methods For Brain Stimulation"), U.S. patent application Ser. No. 12/237,888 ("Leads With Non-Circular-Shaped Distal Ends For Brain Stimulation Systems and Methods of Making and Using"), U.S. Patent Application Publication No. 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, and U.S. Patent Application Publication No. 2009/0187222 A1. Each of these references is incorporated herein by reference in its respective entirety.

Figure 1:
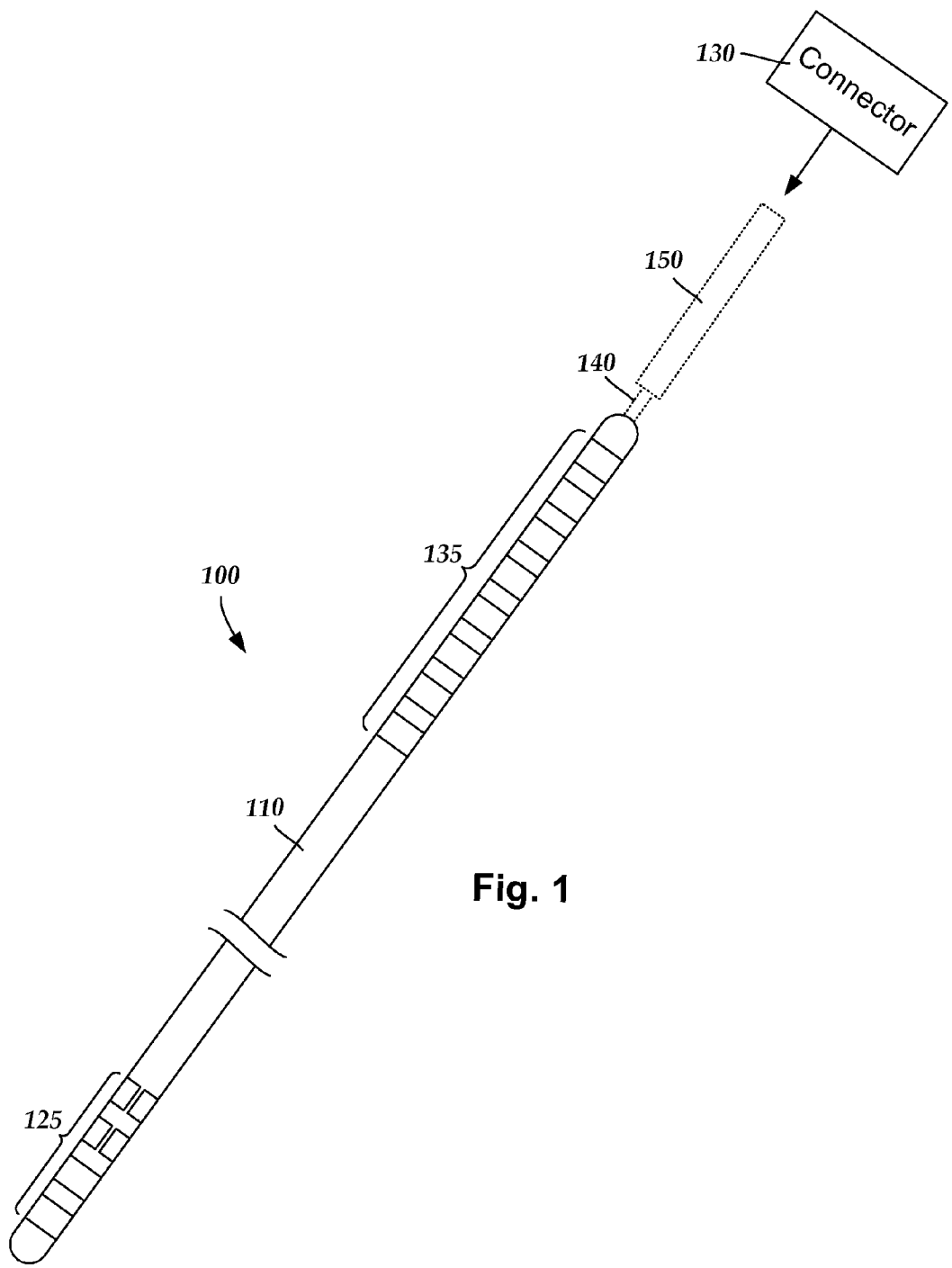
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more than eight stimulation channels (e.g., 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed to one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized additionally or alternatively. Though the following description discusses stimulation electrodes, it will be understood that all configurations of the stimulation electrodes discussed may be utilized in arranging recording electrodes as well.

Figure 2:
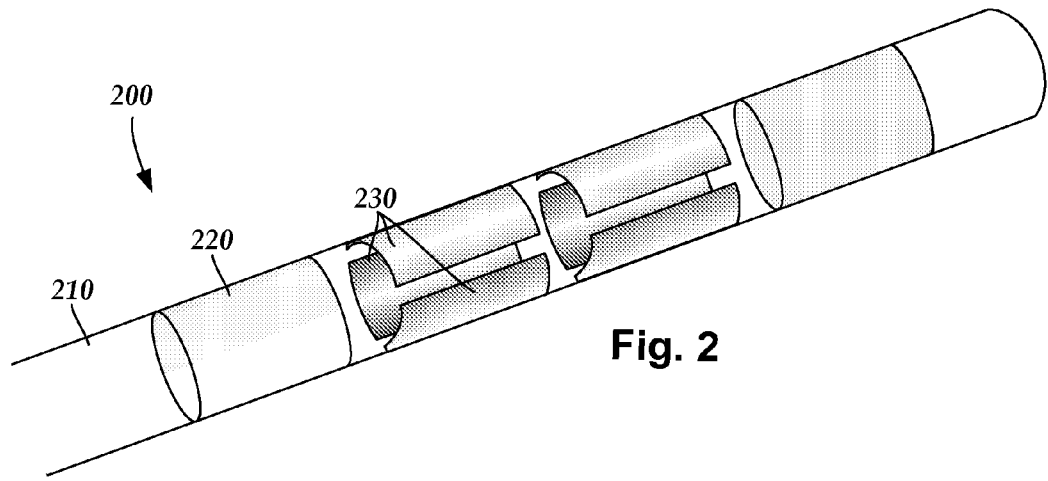
FIG. 2 is a schematic perspective view of one embodiment of a portion of a lead having a plurality of segmented electrodes, according to the invention.

FIG. 2 illustrates one embodiment of a distal portion of a lead 200 for brain stimulation. The lead 200 includes a lead body 210, one or more optional ring electrodes 220, and a plurality of sets of segmented electrodes 230. The lead body 210 can be formed of a biocompatible, non-conducting material such as, for example, a polymeric material. Suitable polymeric materials include, but are not limited to, silicone, polyurethane, polyethylene, polyurea, polyurethane-urea, or the like. Once implanted in the body, the lead 200 may be in contact with body tissue for extended periods of time. In at least some embodiments, the lead 200 has a cross-sectional diameter of no more than 1.5 mm and may be in the range of 1 to 1.5 mm. In at least some embodiments, the lead 200 has a length of at least 10 cm and the length of the lead 200 may be in the range of 25 to 70 cm.

The stimulation electrodes may be made using a metal, alloy, conductive oxide, or any other suitable conductive biocompatible material. Examples of suitable materials include, but are not limited to, platinum, platinum iridium alloy, iridium, titanium, tungsten, palladium, or the like. Preferably, the stimulation electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 220 may be disposed on any part of the lead body 210, usually near a distal end of the lead 200. In FIG. 2, the lead 200 includes two ring electrodes 220. Any number of ring electrodes 220 may be disposed along the length of the lead body 210 including, for example, one, two three, four, five, six, seven, eight, nine, ten, eleven, twelve, thirteen, fourteen, fifteen, sixteen or more ring electrodes 220. It will be understood that any number of ring electrodes may be disposed along the length of the lead body 210. In some embodiments, the ring electrodes 220 are substantially cylindrical and wrap around the entire circumference of the lead body 210. In some embodiments, the outer diameters of the ring electrodes 220 are substantially equal to the outer diameter of the lead body 210. The length of the ring electrodes 220 may vary according to the desired treatment and the location of the target neurons. In some embodiments the length of the ring electrodes 220 are less than or equal to the diameters of the ring electrodes 220. In other embodiments, the lengths of the ring electrodes 220 are greater than the diameters of the ring electrodes 220.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

In FIG. 2, the lead 200 is shown having a plurality of segmented electrodes 230. Any number of segmented electrodes 230 may be disposed on the lead body 210 including, for example, one, two three, four, five, six, seven, eight, nine, ten, eleven, twelve, thirteen, fourteen, fifteen, sixteen or more segmented electrodes 230. It will be understood that any number of segmented electrodes 230 may be disposed along the length of the lead body 210.

The segmented electrodes 230 may be grouped into sets of segmented electrodes, where each set is disposed around a circumference of the lead 200 at a particular longitudinal axis of the lead 200. The lead 200 may have any number segmented electrodes 230 in a given set of segmented electrodes. The lead 200 may have one, two, three, four, five, six, seven, eight, or more segmented electrodes 230 in a given set. In at least some embodiments, each set of segmented electrodes 230 of the lead 200 contains the same number of segmented electrodes 230. The segmented electrodes 230 disposed on the lead 200 may include a different number of electrodes than at least one other set of segmented electrodes 230 disposed on the lead 200.

The segmented electrodes 230 may vary in size and shape. In some embodiments, the segmented electrodes 230 are all of the same size, shape, diameter, width or area or any combination thereof. In some embodiments, the segmented electrodes 230 of each circumferential set (or even all segmented electrodes disposed on the lead 200) may be identical in size and shape.

Each set of segmented electrodes 230 may be disposed around the circumference of the lead body 210 to form a substantially cylindrical shape around the lead body 210. The spacing between individual electrodes of a given set of the segmented electrodes may be different from the spacing between individual electrodes of another set of segmented electrodes on the lead 200. In at least some embodiments, equal spaces, gaps or cutouts are disposed between each segmented electrode 230 around the circumference of the lead body 210. In other embodiments, the spaces, gaps or cutouts between the segmented electrodes 230 may differ in size or shape. In other embodiments, the spaces, gaps, or cutouts between segmented electrodes 230 may be uniform for a particular set of the segmented electrodes 230, or for all sets of the segmented electrodes 230. The segmented electrodes 230 may be positioned in irregular or regular intervals along a length the lead body 210.

Conductors (see e.g., conductors 640 of FIG. 6) that attach to the ring electrodes 220 or segmented electrodes 230 extend along the lead body 210. These conductors may extend through the material of the lead 20 or along one or more lumens defined by the lead 200, or both. The conductors are presented at a connector (via terminals) for coupling of the electrodes 220, 230 to a control unit (not shown). In at least some embodiments, the stimulation electrodes 220, 230 correspond to wire conductors that extend out of the lead body 210 and are trimmed or ground down flush with an outer surface of the lead 200.

Figure 3A:
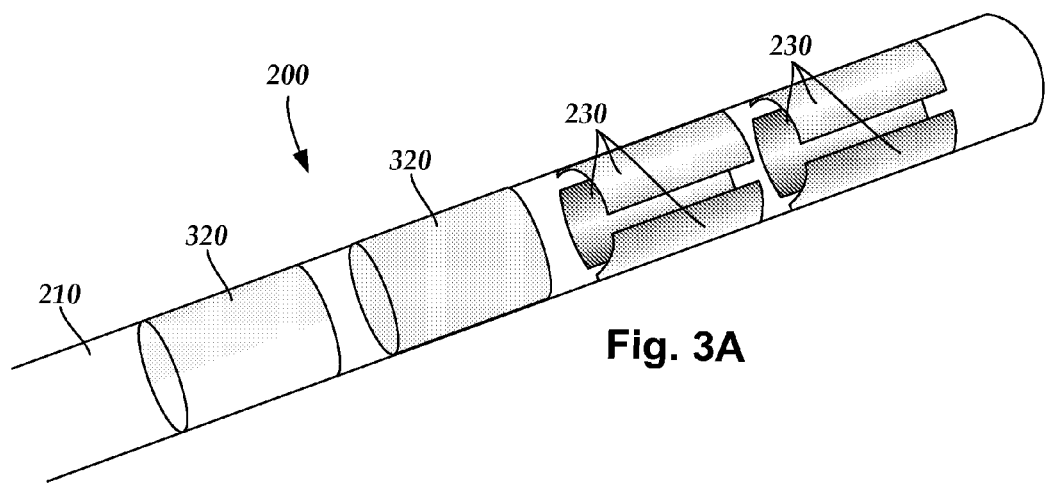
FIG. 3A is a perspective view of a third embodiment of a portion of a lead having a plurality of segmented electrodes, according to the invention.
Figure 3B:
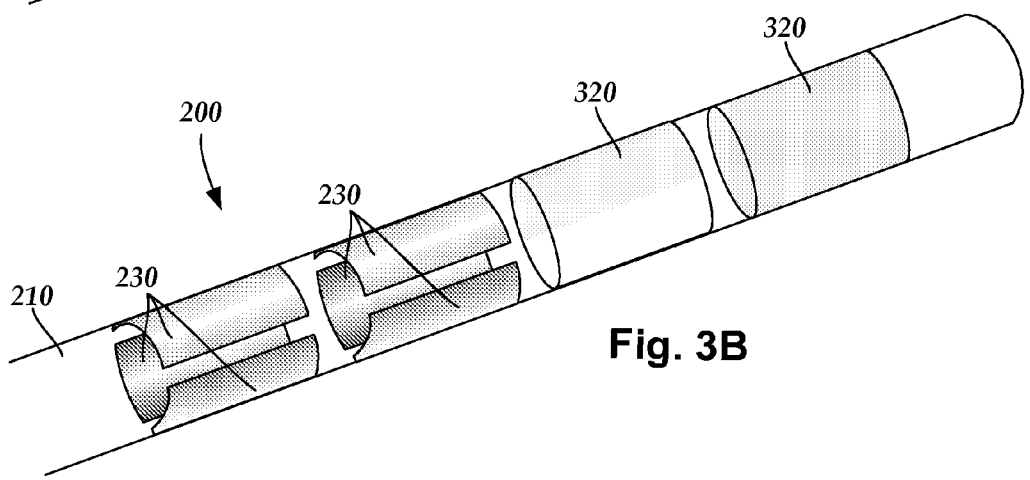
FIG. 3B is a perspective view of a fourth embodiment of a portion of a lead having a plurality of segmented electrodes, according to the invention.

When the lead 200 includes both ring electrodes 220 and segmented electrodes 230, the ring electrodes 220 and the segmented electrodes 230 may be arranged in many different configurations. For example, when the lead 200 includes two sets of ring electrodes 220 and two sets of segmented electrodes 230, the ring electrodes 220 can flank the two sets of segmented electrodes 230 (see e.g., FIG. 2). Alternately, the two sets of ring electrodes 220 can be disposed proximal to the two sets of segmented electrodes 230 (see e.g., FIG. 3A), or the two sets of ring electrodes 220 can be disposed distal to the two sets of segmented electrodes 230 (see e.g., FIG. 3B). It will be understood that other configurations are possible as well (e.g., alternating ring and segmented electrodes, or the like).

By varying the location of the segmented electrodes 230, different coverage of the target neurons may be selected. For example, the electrode arrangement of FIG. 3A may be useful if the physician anticipates that the neural target will be closer to a distal tip of the lead body 210, while the electrode arrangement of FIG. 3B may be useful if the physician anticipates that the neural target will be closer to a proximal end of the lead body 210.

Any combination of ring electrodes 220 and segmented electrodes 230 may be disposed on the lead 200. For example, the lead may include a first ring electrode 120, two sets of segmented electrodes, each set formed of three segmented electrodes 230, and a final ring electrode 120 at the end of the lead. This configuration may simply be referred to as a 1-3-3-1 configuration. It may be useful to refer to the electrodes with this shorthand notation. Thus, the embodiment of FIG. 3A may be referred to as a 1-1-3-3 configuration, while the embodiment of FIG. 3B may be referred to as a 3-3-1-1 configuration. Other eight-electrode configurations include, for example, a 2-2-2-2 configuration, where four sets of segmented electrodes are disposed on the lead, and a 4-4 configuration, where two sets of segmented electrodes, each having four segmented electrodes 230 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 4:
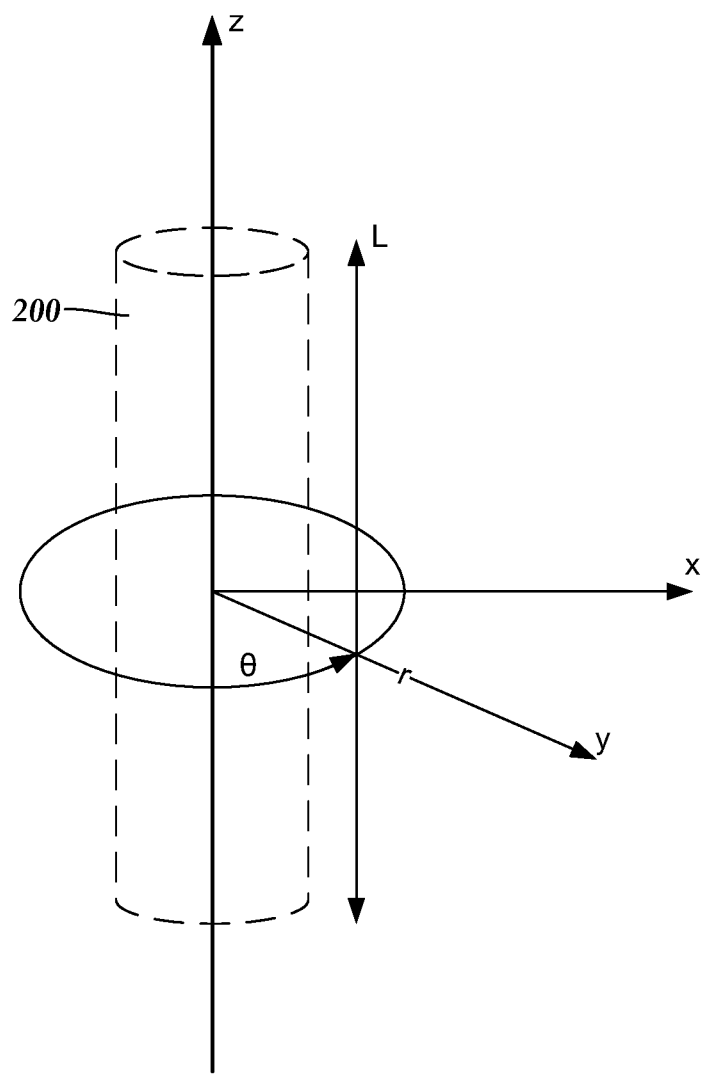
FIG. 4 is a schematic diagram of radial current steering along various electrode levels along the length of a lead, according to the invention.

FIG. 4 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle $\theta$ around the circumference of the lead 200 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes allows the centroid of stimulation to be shifted to a variety of different locations along the lead 200.

As can be appreciated from FIG. 4, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 200 includes a plurality of sets of segmented electrodes 230, it may be desirable to form the lead 200 such that corresponding electrodes of different sets of segmented electrodes 230 are radially aligned with one another along the length of the lead 200 (see e.g., the segmented electrodes 230 shown in FIG. 2). Radial alignment between corresponding electrodes of different sets of segmented electrodes 230 along the length of the lead 200 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 200 are radially aligned with one another and do not radially shift in relation to one another during manufacturing of the lead 200.

Figure 5:
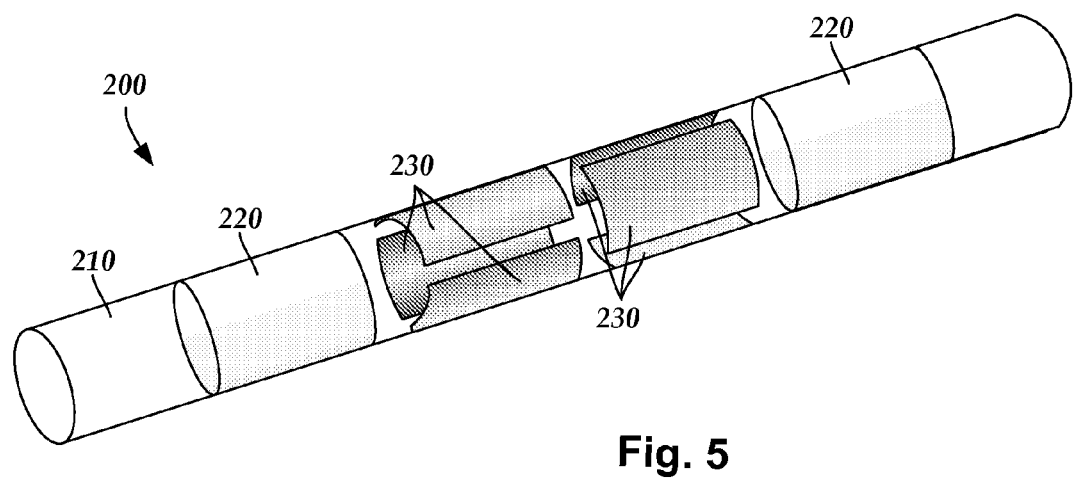
FIG. 5 is a perspective view of another embodiment of a portion of a lead having a plurality of segmented electrodes arranged in a staggered orientation, according to the invention.

FIG. 5 is a side view of another embodiment of the lead 200 having a plurality of sets of segmented electrodes. As shown in FIG. 5, individual electrodes in the two sets of segmented electrodes 230 are staggered relative to one another along the length of the lead body 210. In some cases, the staggered positioning of corresponding electrodes of different sets of segmented electrodes along the length of the lead 200 may be designed for a specific application.

Corresponding electrodes of at least two different sets of segmented electrodes can be radially aligned with one another along the length of the lead by disposing tabs on at least some of the electrodes and stringing an elongated member (e.g., one or more conductors, or the like) through one or more guides formed in one or more of the tabs disposed along different sets of the segmented electrodes. Corresponding electrodes of different sets of segmented electrodes can be radially aligned with one another along the length of the lead by disposing one or more electrode on membranes configured and arranged to couple to the lead. It will be understood that radially-aligning segmented electrodes along the length of the lead can applied to either all, or only some, of the total number of segmented electrodes disposed on the lead.

Figure 6:
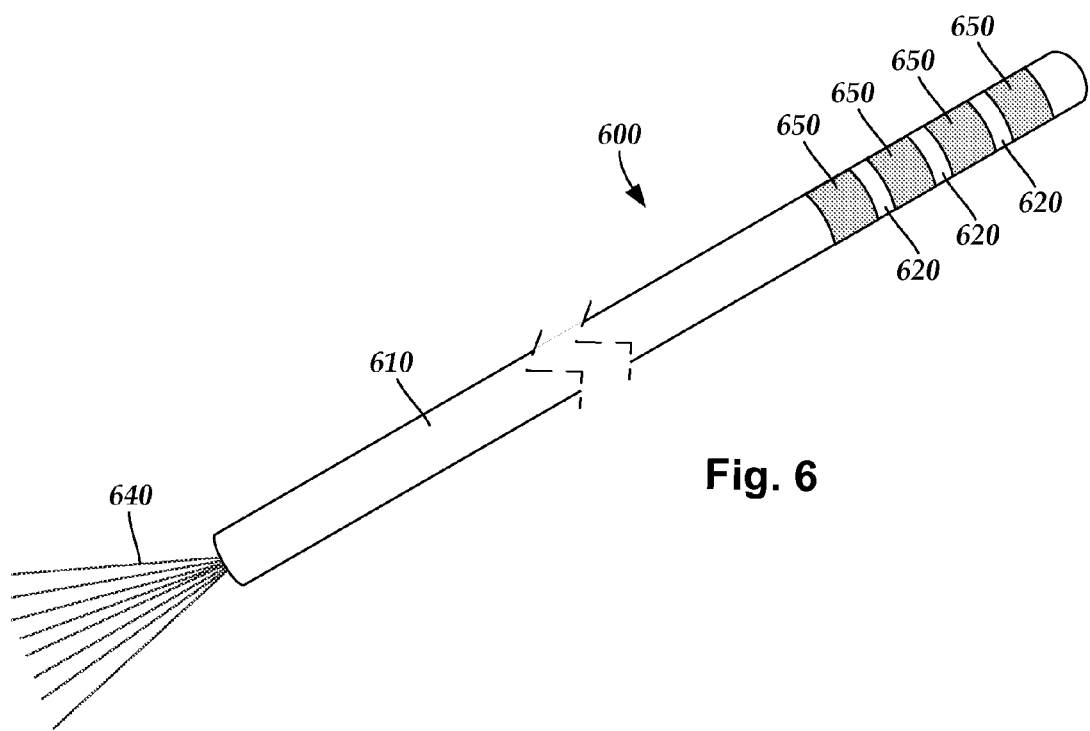
FIG. 6 is a perspective view of a portion of one embodiment of a lead having conductors exposed at the proximal end, according to the invention.

In at least some embodiments, tabbed segmented electrodes are formed using ring electrodes that are ground down prior to operation of the lead 200. A brief description of one embodiment of a lead fabrication process is described below, with respect to FIGS. 6-10. FIG. 6 is a perspective view of a portion of a lead 600 having conductors 640 extending along the length of the lead body 610 from a proximal end of the lead body 610 to pre-electrodes 650. In at least some embodiments, the pre-electrodes 650 are disposed at a distal end of a lead body 610. Non-conductive spacers 620 may be disposed between the pre-electrodes 650.

As described above with reference to FIG. 2, the conductors 640 attach to the pre-electrodes 650 and extend along the lead body 610, either through the material of the lead 600, or along one or more lumens defined by the lead 600, or both. In some embodiments, the stimulation or recording electrodes correspond to wire conductors that extend out of the lead body 610 and that are trimmed or ground down flush with an outer surface of the lead 600. The conductors 640 may further be coupled to terminals (not shown). The terminals are typically disposed at the proximal end of the one or more lead bodies for connection to corresponding connector contacts in connectors disposed on, for example, a control module (or to other devices, such as connector contacts on a lead extension, an operating room cable, or a lead adaptor). Furthermore, the control module may provide stimulation current, often in the form of pulses, to the stimulation electrodes. The length of the lead body 610 and the pre-electrodes 650 exposed at the distal end may vary as required for the final product configuration.

Figure 7:
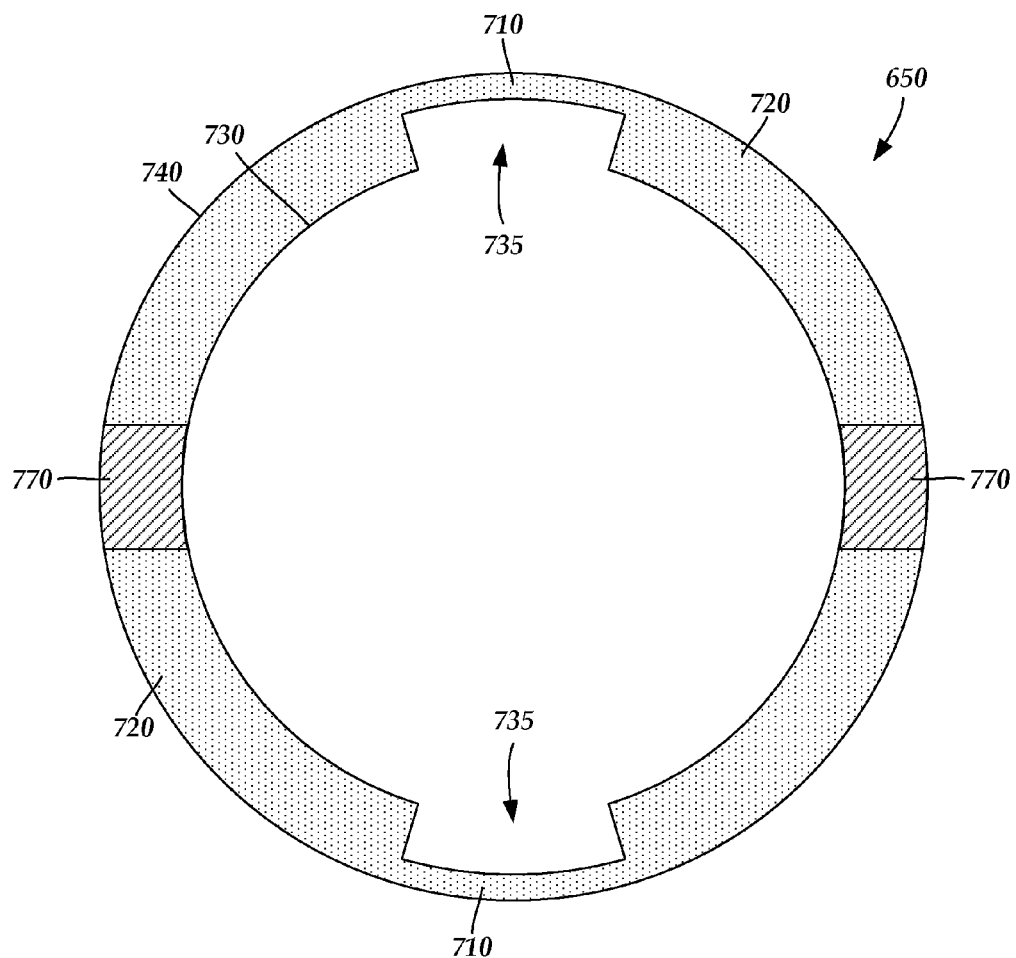
FIG. 7 is a schematic cross-sectional view of one embodiment of a pre-electrode having two thin-walled portions separated from one another by two thick-walled portions, according to the invention.

In some embodiments, fabrication of an electrode array that includes segmented electrodes begins with the pre-electrode 650, from which segmented electrodes are formed. FIG. 7 is a schematic transverse cross-sectional view of one of the pre-electrodes 650. In some embodiments, as seen in FIG. 7, the pre-electrode 650 has two radially-spaced-apart thin-walled portions 710 radially separated from one anther by two thick-walled portions 720. The thin-walled portions 710 and thick-walled portions 720 may be formed to include an inner surface 730 and an outer surface 740. In some embodiments, the outer surface 740 is isodiametric, while the inner surface 730 is not isodiametric. Instead, the inner surface 730 may include one or more keyed portions 735 where the inner surface 730 is larger than the remaining portions, or where portions of the pre-electrode 700 have been removed, or are unformed. It will be understood that the keyed portions 735 may be formed with a sudden change in diameter (as shown in FIG. 7) or a more gradual change in diameter.

The resulting thin-walled portions 710 and thick-walled portions 720 may vary in size. In some embodiments, the thin-walled portions 710 and thick-walled portions 720 are of equal radial length. In at least some other embodiments, the majority of the circumference of the pre-electrode 650 forms the thick-walled portions 720. As seen in FIG. 7, in some embodiments, two thick-walled portions 720 and two thin-walled portions 710 are formed. In some embodiments, the thin-walled portions 710 are of equal radial length. In some embodiments, the thick-walled portions 720 are of equal radial length. It will be understood that in at least some other embodiments, one thick-walled portion may be formed larger than another thick-walled portion.

The lead body 610 may include ablated sections for receiving the pre-electrodes 650. In some embodiments, the ablated sections of the lead body 610 are disposed on the distal end of the lead body 610, particularly portions of the lead body 610 disposed under the pre-electrodes 650. In some embodiments, slots, grit, sand-blasted or roughened regions, or a coating such as titanium nitride may be added to the pre-electrodes 650, in particular the inner diameter 730, to increase adhesion to the leady body 610.

Conductors (640 of FIG. 6) may be coupled to the pre-electrodes 650. In some embodiments, the conductors 640 are welded to the pre-electrodes 650, though it will be understood that any suitable method of coupling the pre-electrodes 650 to the conductors 640 may be utilized, such as laser welding, resistance welding, conductive epoxy, crimping, staking, and the like. As seen in FIG. 7, the pre-electrode 650 may include one or more connection elements 770 (e.g., a slot, groove, protrusion, or the like) for facilitating coupling of one or more of the conductors 640 to the pre-electrode 650. In some embodiments, a plurality of connection elements 770 may be disposed on the pre-electrode 650, so that a plurality of conductors 640 are coupled to different portions of the pre-electrode 650. In at least some embodiments, the connection elements 770 are disposed on one or more of the thick-walled portions 720 of the pre-electrode 650, thereby providing locations to couple the thick-walled portions 720 of the pre-electrode 650 to at least one of the conductors 640. Additionally, the one or more connection elements 770 may provide additional adhesion of the segmented electrode sections to the underlying material.

In some embodiments, spacers (620 in FIG. 6) have hollow center areas such that the spacers 620 can be threaded onto the lead body 610 or can be used as a part of the lead body 610 to separate the electrodes. The lead 600 may also include an end spacer (not shown). The end spacer is disposed at the distal end of the lead 600. The end spacer may have any shape, but is preferably rounded at the distal end, or is rounded in a post-processing forming step. The spacers 620 and the end spacer can be made of any non-conductive biocompatible material including, for example, silicone, polyurethane, and polyetheretherketone (PEEK). The spacers 620 facilitate electrical isolation of the pre-electrodes 650. Additionally or alternatively, the pre-electrodes 650 can be disposed over portions of a contiguous, non-conducting lead body 610 with an opening through the lead body 610 to allow the conductors 640 to be coupled to the pre-electrodes 650.

In some embodiments, the outer surface 740 of the pre-electrodes 650 may be equal in diameter to an outer surface of the spacers 620. In some other embodiments, the outer surface 740 of the pre-electrodes 650 may alternatively be greater in diameter than the outer surface of the spacers 620 such that the pre-electrodes 650 are raised above the spacers 620. Alternatively, the outer surface 740 of the pre-electrodes 650 may alternatively be smaller in diameter than the outer surface of the spacers 620 such that the pre-electrodes 650 are recessed.

An assembly may be subject to a reflow operation after all the spacers 620 and pre-electrodes 650 have been loaded onto the lead body 610 and attached to conductors 640, as necessary. The reflow operation is useful in attaching the spacers 620 and pre-electrodes 650 to the lead body 610 and improves structural integrity of the assembly and leads to improved reliability. "Reflow", as used herein, includes forcing liquid insulating materials into crevices and spaces not occupied by the pre-electrodes and spacers. One way of forcing the material to occupy void space is to inject the reflow material between the crevices and spaces. The reflow material, which is an insulator, may be the same or different material than the spacers. Alternatively a molding or casting process can be used to fill the voids with one or more insulating materials.

The lead 600 may then be further processed to remove portions of the pre-electrodes 650. In some embodiments, the lead 600 is centerless ground to remove portions of the outer surface 740. It will be understood that any suitable method can be used to remove these portions including cutting, skiving or laser ablation. In at least some embodiments, portions of the outer surface 740 of the pre-electrodes 650 are removed until the thin-walled portions 710 of the pre-electrode are completely removed from the pre-electrode 650, thereby resulting in a set of segmented electrodes.

Figure 8:
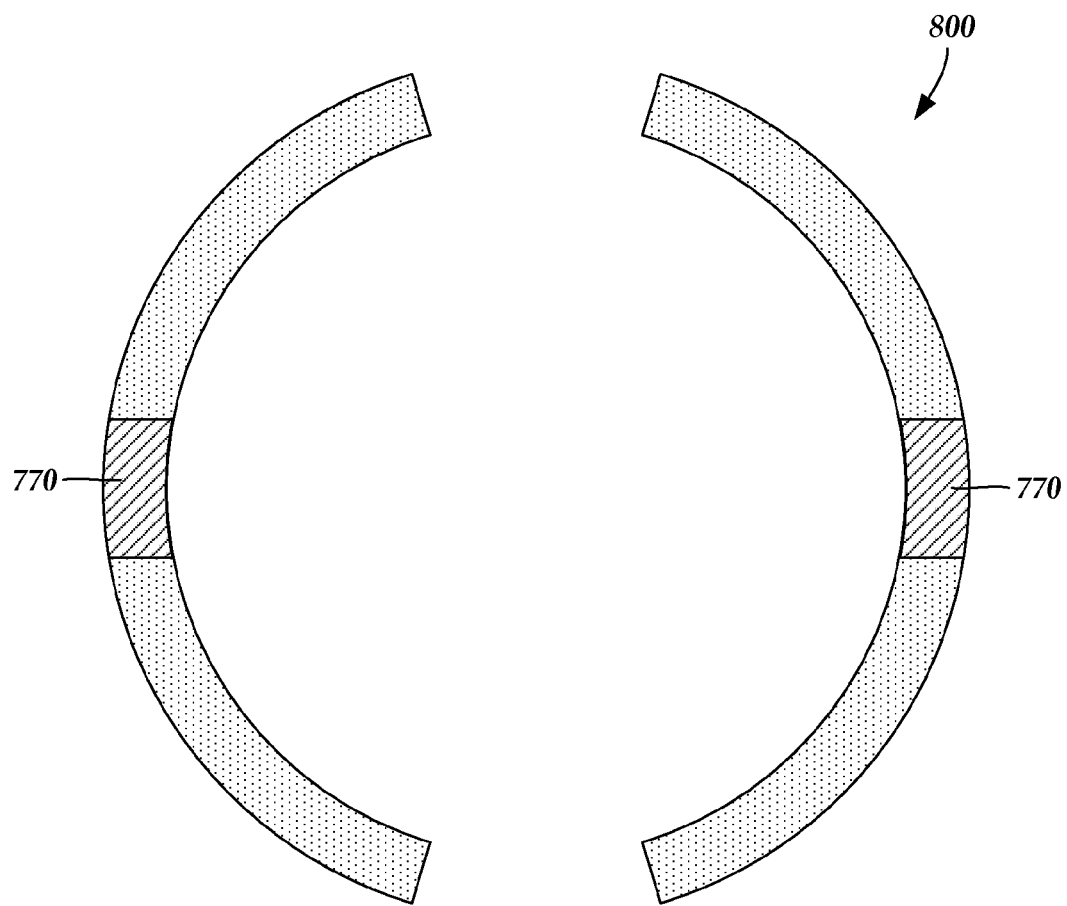
FIG. 8 is a schematic cross-sectional view of one embodiment of the pre-electrode of FIG. 7 after the thin-walled portions have been removed to form two segmented electrodes, according to the invention.

FIG. 8 is a schematic cross-sectional view of the pre-electrode 650 of FIG. 7 after the thin-walled portions 710 have been removed. As seen in FIG. 8, the result of removing the thin-walled portions is that two segmented electrodes 800 are formed. Thus, the thin-walled portions 710 and thick-walled portions 720 may be arranged so that any configuration of segmented electrodes 800 is formed after grinding. As discussed above, in at least some embodiments the connection elements 770 are arranged such that each segmented electrode 800 is connected to at least one of the conductors 640 after the grinding process.

Figure 9:
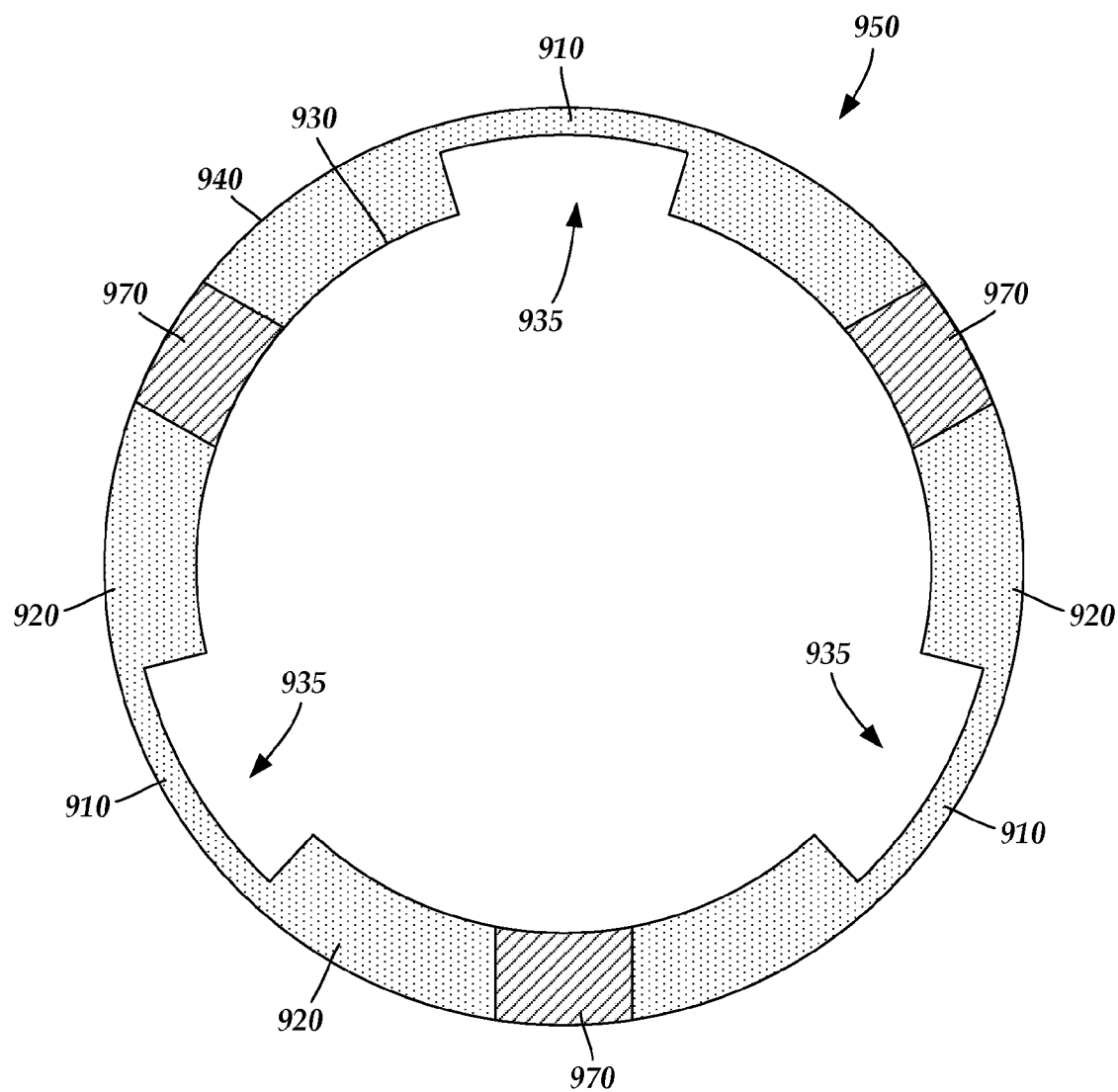
FIG. 9 is a schematic cross-sectional view of one embodiment of a pre-electrode having three thin-walled portions separated from one another by three thick-walled portions, according to the invention.

FIG. 9 is a schematic cross-sectional view of a pre-electrode 950 having three thin-walled portions 910 separated by three thick-walled portions 920. The pre-electrode 950 has an inner surface 930 and an outer surface 940. As seen in FIG. 9, the inner surface 930 has three keyed portions 935. As seen in FIG. 9, the pre-electrode 950 may include one or more connection elements 970 (e.g., a slot, groove, protrusion, or the like) for facilitating coupling of one or more of the conductors (640 in FIG. 6) to the pre-electrode 950.

Figure 10:
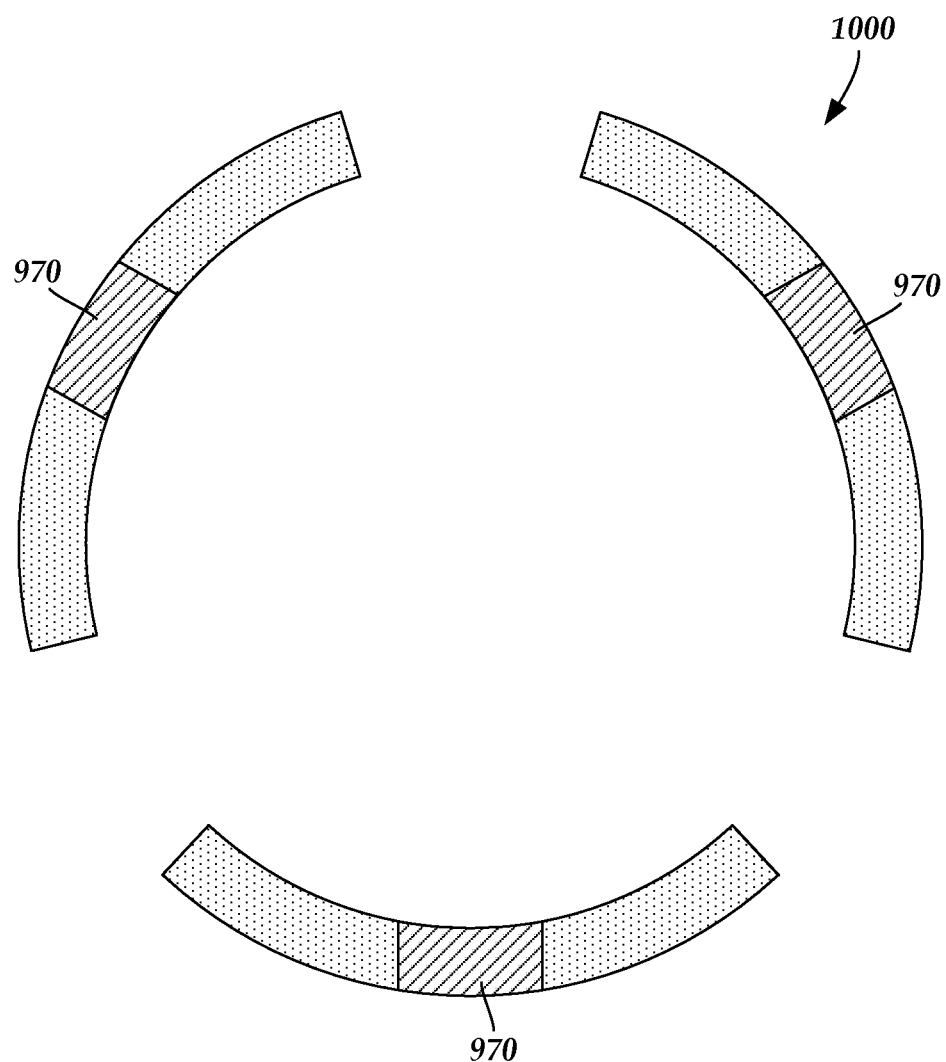
FIG. 10 is a schematic cross-sectional view of one embodiment of the pre-electrode of FIG. 9 after the thin-walled portions have been removed to form three segmented electrodes, according to the invention.

FIG. 10 is a schematic cross-sectional view of a set of three segmented electrodes 1000 formed from the pre-electrode 950 after the thin-walled portions 910 of the pre-electrodes 950 are removed using the methods described above. In some embodiments, the three segmented electrodes 1000 are of the same size. In at least some other embodiments, the keyed portions 935 are arranged such that segmented electrodes 1000 of different sizes are produced after the grinding process. It will be understood that any number of segmented electrodes may be formed in this manner including, for example, two, three, four, five, six, seven, eight, nine, ten, eleven, twelve, thirteen, fourteen, fifteen, sixteen or more radially-arranged segmented electrodes 1000.

In at least some embodiments, one or more tabs are disposed on each of at least two pre-electrodes disposed along a length of the lead. In at least some embodiments, at least one of the one or more tabs disposed on each of the pre-electrodes includes a guide feature for facilitating alignment of multiple guide features along the length of the lead. In at least some embodiments, the one or more tabs are disposed over one of the thick-walled portions of the pre-electrode such that, upon removal of portions of the outer surface of the pre-electrode, the tab is positioned on one of the segmented electrodes. In at least some embodiments, the one or more tabs are coupled to the thick-walled portions of the pre-electrodes such that the one or more tabs do not interfere with connection elements disposed on the pre-electrodes for attaching conductors to subsequently formed segmented electrodes.

Figure 11:
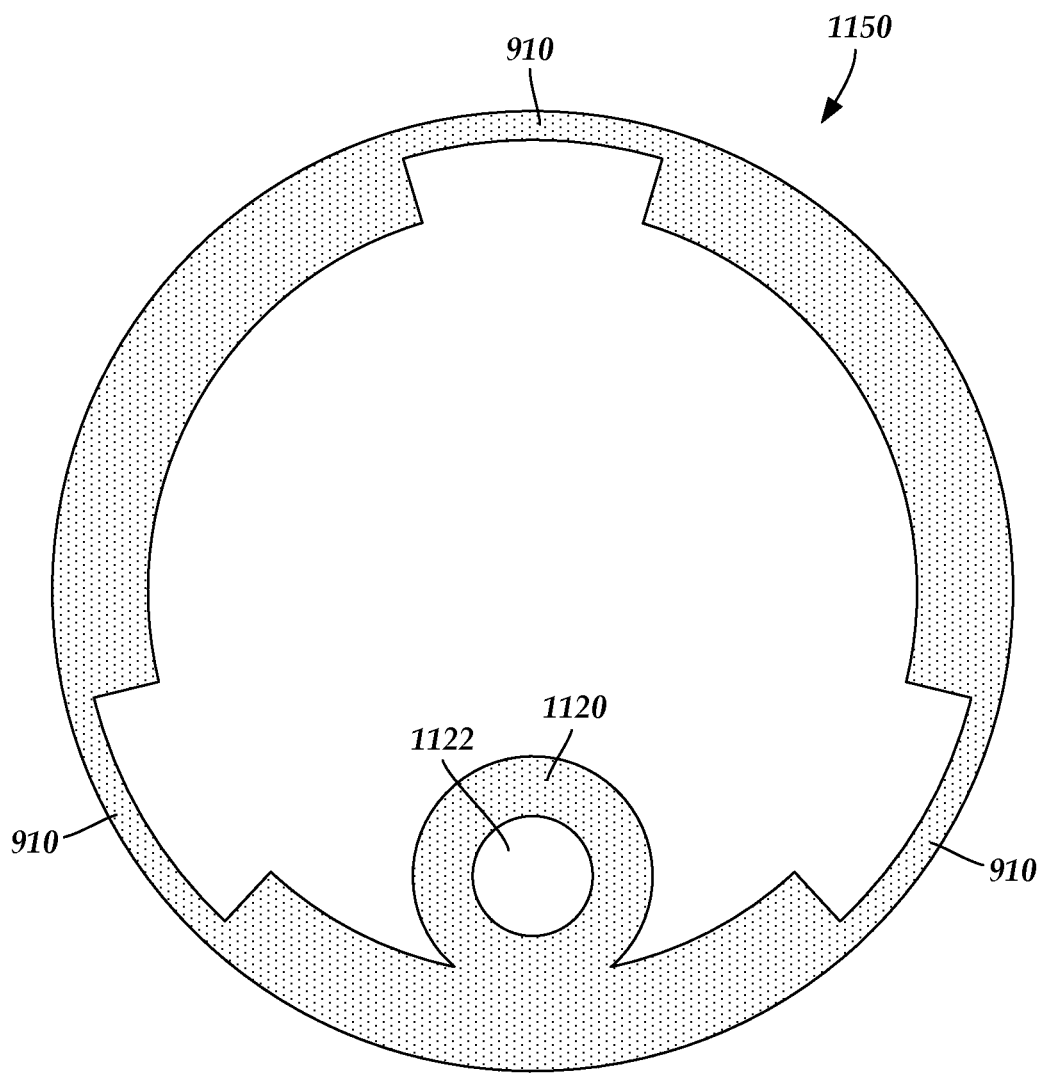
FIG. 11 is a schematic front view of one embodiment of a pre-electrode with tabs disposed over thick-walled portions of the pre-electrode, one of the tabs including a guide feature, according to the invention.

FIG. 11 is a schematic front view of one embodiment of a pre-electrode 1150 with a tab 1120 disposed over one of the thick-walled portions of the pre-electrode 1150. In FIG. 11, the tab 1120 is positioned on the pre-electrode 1150 such that the tab 1120 extends inward from an arc of the pre-electrode 1150. In at least some embodiments, the tab 1120 is positioned on a front surface of the pre-electrode 1150 such that the tab 1120 does not interfere with the coupling of conductors (see e.g., conductors 640) to the pre-electrode 1150. In at least some embodiments, the tab 1120 is positioned on the pre-electrode 1150 such that the tab 1120 is disposed on different sides of the thick-walled portions of the pre-electrode 1150 from the connection elements (770 in FIGS. 7,8; and 970 in FIGS. 9,10). The tab 1120 can be formed from any suitable material. In preferred embodiments, the tab 1120 is formed from the same material as the pre-electrode 1150.

In FIG. 11, one tab 1120 is disposed on one of the thick-walled portions of the pre-electrode 1150. Alternately, a plurality of tabs 1120 can be disposed on one of the thick-walled portions of the pre-electrode 1150. In at least some embodiments, at least one tab 1120 is disposed on a plurality of thick-walled portions of the pre-electrode 1150.

Optionally, the tab 1120 includes a guide feature 1122. In FIG. 11, the guide feature 1122 is an aperture defined in the tab 1120. The lead 600 includes at least two pre-electrodes 1150, with each of the at least two pre-electrodes 1150 including at least one tab 1120 (and, optionally, at least one guide feature 1122).

The guide feature 1122 is configured and arranged to facilitate alignment of the tab on which the guide feature 1122 is disposed with at least one other corresponding guide feature 1122 disposed on a corresponding tab 1120 of another of the pre-electrodes 1150 of the lead. The guide feature 1122 can be formed as any shape of material configured and arranged to at least partially retain an elongated member (e.g., one or more of the conductors 640, or the like) extending to the tab including, for example, an aperture defined in the tab; or a hook, a clip, or the like disposed on the tab.

In at least some embodiments, one or more elongated members extend along at least a portion of the length of the lead 600 such that at least one of the one or more elongated members extends through the guide features 1122 of each of at least two pre-electrodes 1150. When the one or more elongated members extend through two or more guide features, where each of the guide features is disposed on a different pre-electrode, the two or more corresponding pre-electrodes 1150 can align along the length of the lead 600, thereby aligning the respective pre-electrodes 1150 upon which the guide features 1122 are disposed (see e.g., the segmented electrodes 230 of FIG. 2). In at least some embodiments, at least one of the one or more elongated members is one of the conductors (see e.g., conductors 640 of FIG. 6). In at least some embodiments, the one or more elongated members that extend through the guide feature 1122 of the tab 1120 includes the same connector that will subsequently electrically couple to the segmented electrode (1230*a* of FIG. 12) and extend to the proximal end of the lead 600, as shown in FIG. 6.

It will be understood that additional guide features can be disposed on one or more of the tabs 1120 of two more pre-electrodes 1150 to provide additional alignment features that can be used in conjunction with other elongated members (e.g., other conductors) to provide redundant alignment between pre-electrodes 1150, if desired.

In at least some embodiments, once the one or more elongated members are extended through the guide features 1122 of the pre-electrodes 1150 and the pre-electrodes 1150 are aligned with one another, the tabs 1120 can be molded in place over the lead 600 to ensure that the pre-electrodes 1150 do not undergo radial shifting during subsequent assembly and manufacturing. As discussed above with reference to FIG. 7, when the pre-electrode 1150 is disposed on the lead 600, the lead 600 can be centerless ground (or cut, skived, laser ablated, or the like) to remove portions of the outer diameter (e.g., to remove the thin-walled portions) so that only the thick-walled regions (the segmented-electrode portions) of the pre-electrode remain.

Figure 12:
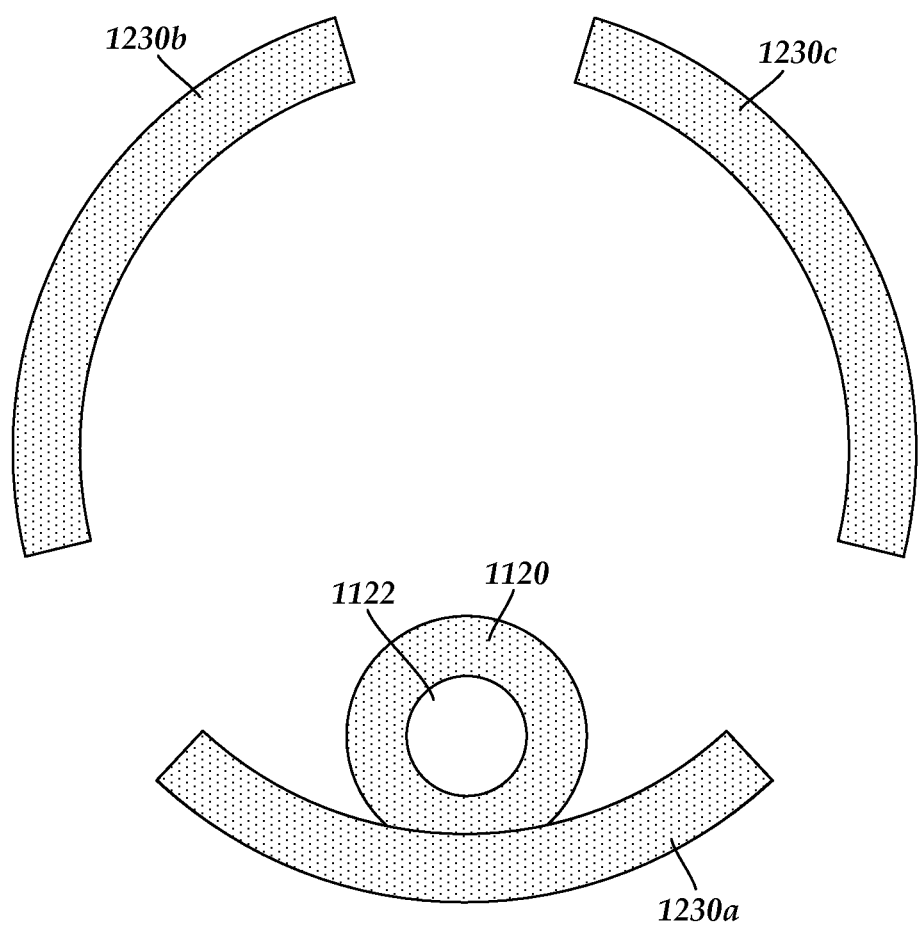
FIG. 12 is a schematic rear view of one embodiment of the pre-electrode of FIG. 11 after thin-walled portions of the pre-electrode have been removed to form three segmented electrodes with tabs, one of the tabs including a guide feature, according to the invention.

FIG. 12 is a schematic back view of one embodiment of the pre-electrode 1150 after the thin-walled portions have been removed to create three segmented electrodes 1230*a*, 1230*b*, 1230*c*. In FIG. 12, the tab 1120 is disposed on 1230*a*. As discussed above, in at least some embodiments, corresponding electrodes of different sets of segmented electrodes are radially aligned with one another along the length of the lead by disposing tabs on at least some of the electrodes and stringing an elongated member (e.g., one or more conductors, or the like) through one or more guides formed in one or more of the tabs disposed along different sets of the segmented electrodes.

Turning to FIG. 13A, in at least some alternate embodiments, corresponding electrodes of different sets of segmented electrodes can be radially aligned with one another along the length of the lead by first disposing electrodes on a membrane, and then coupling the membrane to the lead such that the electrodes disposed on the membrane form radially-aligned electrodes disposed along the length of the lead. FIG. 13A is a schematic top view of one embodiment of a membrane 1302 that is configured and arranged to receive electrodes and that is configured and arranged for being disposed on the lead 600. FIG. 13B is a schematic side view of one embodiment of the membrane 1302.

In FIGS. 13A and 13B, the membrane 1302 is shown in a substantially planar configuration with a front face 1302*a*, a rear face 1302*b*, and a width 1304. The membrane 1302 is configured and arranged to be coupled to the lead 600 such that the rear face 1302*b* of the membrane 1302 abuts the outer surface of the lead 600. The membrane 1302 can be configured and arranged to be wrapped around a circumference of the lead 600 such that the membrane 1302 conforms to the shape of the outer surface of the lead 600. In at least some embodiments, the membrane 1302 is configured and arranged to be wrapped around the circumference of the lead 600 such that the width 1304 of the membrane 1302 wraps around the circumference of the lead 600 (e.g., the membrane 1302 is wrapped into a cylinder such that the width 1304 of the membrane becomes the circumference of the cylinder). In at least some embodiments, the width 1304 of the membrane 1304 is equal to the circumference of the lead 600. In alternate embodiments, the width 1304 is less than, or greater than, the circumference of the lead 600. In most cases, the width 1304 of the membrane 1302 is less than a length of the membrane 1302.

The membrane 1302 can be formed from any suitable non-conductive material. It may be an advantage to form the membrane 1302 as thin as possible to avoid unduly increasing the diameter of the lead 600. It may further be an advantage to form the membrane 1302 from one or more flexible materials to facilitate wrapping of the membrane 1302 around the circumference of the lead 600.

The membrane 1302 includes wells 1306 configured and arranged to receive electrodes. In at least some embodiments, the wells 1306 have a depth that is at no less than a thickness of the electrodes. In at least some embodiments, at least one of the wells 1306 includes an adhesive for facilitating coupling of the electrodes to their respective wells 1306. It will be understood that in alternate embodiments, the membrane 1302 does not include wells 1306. In which case, the electrodes can be disposed on the front face 1302*a*.

FIG. 14 is a schematic top view of one embodiment of an array of electrodes 1402 configured and arranged for insertion into the wells 1306. The array of electrodes 1402 includes one or more long electrodes 1402*a* and one or more short electrodes 1402*b*. The long electrodes 1402*a* are configured and arranged to form ring electrodes and the short electrodes 1402*b* are configured and arranged to form segmented electrodes when the electrodes 1402 are coupled to the membrane 1302, and the membrane 1302 is coupled to the lead 600. The array of electrodes 1402 may include as many long electrodes 1402*a* and as many short electrodes 1402*b* as desired. In at least some embodiments, the array of electrodes 1402 includes only short electrodes 1402*b*. In FIG. 14, the number of short electrodes 1402*b* arranged horizontally determines the number of segmented electrodes in a set of segmented electrodes.

The electrodes 1402 can be disposed on the front face 1302*a* of the membrane 1302 in any configuration. In at least some embodiments, at least some of the electrodes 1402*b* are disposed on the membrane 1302 in at least two rows that extend in directions that are parallel with one another and are also parallel with the width 1304 of the membranes 1302. In which case, when the membrane 1302 is coupled to the lead 600 such that the width 1304 of the membrane 1302 is wrapped around the circumference of the lead 600, the electrodes 1402*b* from the at least two rows are disposed around the circumference of the lead 600 such that the electrodes 1402*b* from the at least two rows form sets of segmented electrodes.

In at least some embodiments, individual upper and lower electrodes 1402*b* are part of two sets of segmented electrodes that are vertically aligned with one another on the membrane 1302, as shown in FIG. 14. In which case, when the membrane 1302 is coupled to the lead 600 such that the width 1304 of the membrane 1302 is wrapped around the circumference of the lead 600, the electrodes 1402*b* of those at least two rows form at least two sets of segmented electrodes that are radially-aligned with one another along a length of the lead 600.

The array of electrodes 1402 can be formed in any suitable arrangement. In FIG. 14, the electrodes 1402 are arranged in a 1-3-3-1 arrangement. Any arrangement, however, can be used. In FIG. 14, the electrodes 1402 are divided into equally spaced rows configured and arranged for disposing on the membrane 1302. In at least some embodiments, the rows may be offset from one another such that electrodes 1402 are not longitudinally aligned when disposed on the membrane 1302. The spacing between electrodes 1402 may also vary within rows, or between rows. In at least some other embodiments, the electrodes 1402 can be disposed on the membrane 1302 in a circular arrangement, a diagonal arrangement, or in any other desired pattern.

The electrodes 1402 can be formed from any conductive materials suitable for implantation including, for example, metal, alloy, conductive oxide, or any other suitable conductive biocompatible material. Examples of suitable materials include, but are not limited to, platinum, platinum iridium alloy, iridium, titanium, tungsten, palladium, or the like. In at least some embodiments, the electrodes 1402 are formed from one or more conductive polymers.

Figure 15A:
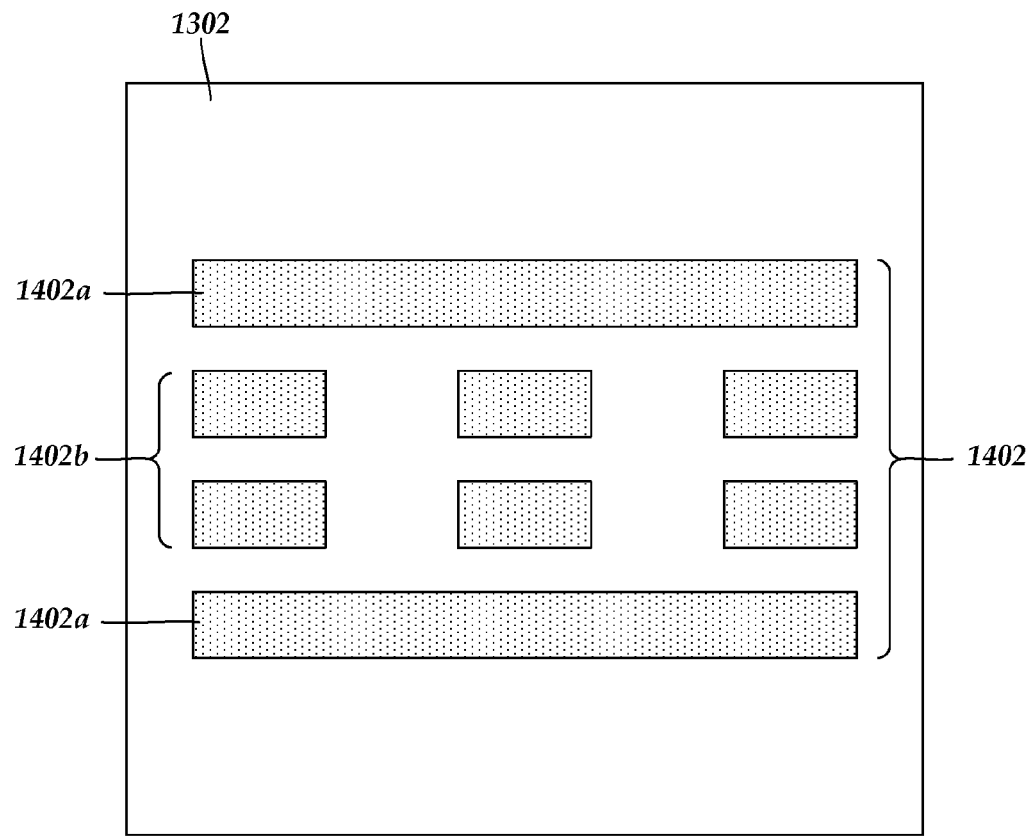
FIG. 15A is a schematic top view of one embodiment of the electrodes of FIG. 14 disposed in wells defined in the membrane of FIG. 13A, according to the invention.
Figure 15B:
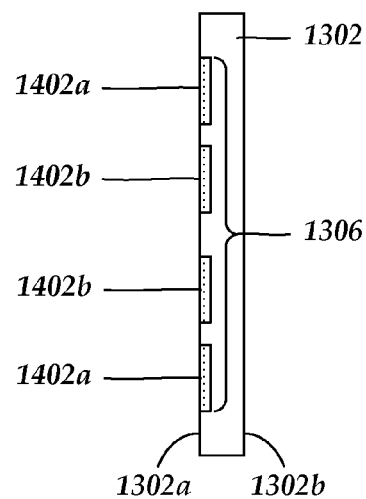
FIG. 15B is a schematic side view of one embodiment of one embodiment of the electrodes of FIG. 14 disposed in wells defined in the membrane of FIG. 13A, according to the invention.

In preferred embodiments, the electrodes 1402 are disposed in the wells 1306 of the membrane 1302 in order to reduce the transverse profile of the portion of the lead 600 that receives the membrane 1302. FIG. 15A is a schematic top view of one embodiment of the array of electrodes 1402 disposed in the wells 1306 of the membrane 1302. FIG. 15B is a schematic side view of one embodiment of the array of electrodes 1402 disposed in the wells 1306 of the membrane 1302. In at least some embodiments, the rear side 1302b of the membrane 1302 includes adhesive to facilitate coupling of the membrane 1302 to the lead 600. When the electrodes 1402 are formed from a flexible enough material, the electrodes may wrap around the lead 600 with the membrane 1302. In at least some embodiments, the electrodes 1402 may additionally be crimped or swaged, or the like, onto the lead 600.

The electrodes 1402 can be coupled to conductors (see e.g., conductors 640 of FIG. 6) in any suitable manner including, for example, laser welding, resistance welding, or the like. In some embodiments, each individual electrode 1402 is connected to a separate and distinct conductor. In at least some other embodiments, multiple electrodes 1402 are connected to the same conductor. In at least some embodiments, the electrodes 1402 are disposed on the front face 1302a of the membrane 1302, either in wells 1306 or not, and coupled to the conductors (see e.g., conductors 640 of FIG. 6) prior to coupling the membrane 1302 to the lead 600. In at least some embodiments, the electrodes 1402 are coupled to the conductors (see e.g., conductors 640 of FIG. 6) along the rear face 1302b of the membrane 1302.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead comprising:
  an elongated lead body having a distal end, a proximal end, a length, a circumference, and an outer surface, the lead body configured and arranged for insertion into a patient;
  a plurality of electrodes disposed along the outer surface of the lead body, the plurality of electrodes comprising at least two sets of segmented electrodes disposed at the distal end of the lead body, each set of segmented electrodes comprising a first segmented electrode and a second segmented electrode spaced apart from one another around the circumference of the lead body;
  a first tab disposed on the first segmented electrode of each of the at least two sets of segmented electrodes, wherein each of the first tabs extends inwardly from the first segmented electrodes into the lead body;
  a guide feature disposed on each of the first tabs, wherein the guide features are each radially aligned with one another along the length of the lead body; and
  a plurality of conductors extending along the length of the lead body from the proximal end to the plurality of electrodes, wherein each of the conductors is electrically coupled to at least one of the plurality of electrodes, wherein one of the plurality of conductors extends through at least two of the radially-aligned guide features of at least two of the plurality of first segmented electrodes.

2. The electrical stimulation lead of claim 1, further comprising a second tab disposed on the second segmented electrode of each of the at least two sets of segmented electrodes, wherein each of the second tabs extend inwardly from the second segmented electrodes into the lead body.

3. The electrical stimulation lead of claim 1, wherein each of the guide features comprises an aperture defined in the first tab.

4. The electrical stimulation lead of claim 1, wherein each set of segmented electrodes further comprises a third segmented electrode radially spaced apart from the first segmented electrode and the second segmented electrode around the circumference of the lead body.

5. The electrical stimulation lead of claim 1, wherein the plurality of electrodes further comprises at least one ring electrode disposed at the distal end of the lead body.

6. The electrical stimulation lead of claim 5, wherein the at least one ring electrode is disposed either proximal or distal to each of the at least two sets of segmented electrodes along the length of the lead body.

7. The electrical stimulation lead of claim 1, further comprising a plurality of terminals disposed at the proximal end of the lead body, wherein each of the conductors is electrically coupled to at least one of the plurality of terminals.

8. An electrical stimulation system comprising:
  the electrical stimulation lead of claim 7; and
  a control module coupled to the proximal end of the electrical stimulation lead, the control module configured and arranged for providing stimulation to the plurality of electrodes.

9. The electrical stimulation system of claim 8, wherein the electrical stimulation lead has at least eight electrodes, and wherein the control module has at least eight stimulation channels, each stimulation channel independently programmable to deliver a stimulus current through each channel.

10. A method of forming a lead for a stimulation device, the method comprising:
  forming a plurality of pre-electrodes, wherein each of the pre-electrodes is formed in the shape of a ring, wherein each of the plurality of pre-electrodes comprises at least two thin-walled portions separated by at least two thick-walled portions, wherein at least two of the plurality of pre-electrodes each comprise a first tab disposed on one of the at least two thick-walled portions, wherein each of the first tabs comprises a guide feature;
  disposing the plurality of pie-electrodes near a distal end of a lead body;
  joining at least one conductor to each thick-walled portion of each of the plurality of pre-electrodes such that at least one of the at least one conductor extends through each of the guide features, thereby radially aligning the guide features along a length of the lead body; and
  grinding the plurality of pre-electrodes to remove the thin-walled portions of each of the plurality of pre-electrode to form a plurality of segmented electrodes from the thick-walled portions of each of the plurality of pre-electrodes.

\* \* \* \* \*